(12) United States Patent
Schneider

(10) Patent No.: US 6,204,244 B1
(45) Date of Patent: Mar. 20, 2001

(54) AMINO ACID COMPOSITIONS AND USE THEREOF IN IMMUNOSUPPRESSION

(75) Inventor: Heinz Schneider, Cordast (CH)

(73) Assignee: Novartis Nutrition AG, Bern (CH)

( * ) Notice: Subject to any disclaimer, the term of this patent is extended or adjusted under 35 U.S.C. 154(b) by 0 days.

(21) Appl. No.: 09/230,873

(22) PCT Filed: Jul. 29, 1997

(86) PCT No.: PCT/EP97/04125

§ 371 Date: Feb. 1, 1999

§ 102(e) Date: Feb. 1, 1999

(87) PCT Pub. No.: WO98/04256

PCT Pub. Date: Feb. 5, 1998

Related U.S. Application Data

(63) Continuation of application No. 08/690,476, filed on Jul. 30, 1996.

(51) Int. Cl.[7] .......................... A61K 38/00; A61K 31/195
(52) U.S. Cl. ................................. 514/9; 514/561
(58) Field of Search ......................... 514/9, 561

(56) References Cited

U.S. PATENT DOCUMENTS 5,290,538  3/1994  Bertermann .
5,656,608  8/1997  Schneider et al. .

FOREIGN PATENT DOCUMENTS

WO 95/29675  11/1995  (WO) .

OTHER PUBLICATIONS

De Nicola, J. Am. Soc. Nephrol., vol. 2, No. 3, 47P, 1991.
Mobb, Renal Fail., vol. 17, No. 2, 175–180, 1992.
Thurman, Transplantation, vol. 63, No. 11, 1661–67, Jun. 1997.
Thurman, Hepatology, vol. 24, No. 4, pt. 2, 434A, Oct. 1996.
Weinberg, Kidney Inst., vol. 52, No. 1, 140–151, Jul. 1997.
Cellular Proliferation and Macrophage Influx Precede Interstitial Fibrosis in Cyclosporine Nephrotoxicity, Kidney International, Young, et al., vol. 48, pp. 439–448, (1995).
Glycine Attenuates Fanconi Syndrome Induced by Maleate or Ifosfamide in Rats, Kidney International, Nissim, et al., vol. 49, pp. 684–695, (1996).
Nephrotoxicity of Immunusuppressive Drugs, Nephrology Dialysis Transplantation, Bennett, et al., vol. 9, (Suppl. 4), pp. 141–145 (1994).
Journal of Clinical Investigation, Inc. vol. 92, Oct. 1993, 1859–1865.*

* cited by examiner

Primary Examiner—Zohreh Fay
(74) Attorney, Agent, or Firm—Gabriel Lopez

(57) ABSTRACT

The present invention provides for the use glycine in the preparation of a medicament or nutritional formulation for the prophylaxis and/or therapy of renal dysfunction induced by cyclosporins or ascomycins.

12 Claims, 5 Drawing Sheets

Neutrophils

AMINO ACID COMPOSITIONS AND USE THEREOF IN IMMUNOSUPPRESSION

This Application is a continuation of U.S. Ser. No. 08/690,476, filed Jul. 30, 1996, now pending.

The present invention relates to the use of glycine in the preparation of a medicament or nutritional formulation which may be therapeutically administered to patients to prophylactically and/or therapeutically treat renal dysfunction induced by substances belonging to the classes of cyclosporins and/or ascomycins.

Cyclosporins comprise a class of structurally distinct, cyclic, polyN-methylated undecapeptides, generally possessing immunosuppressive, anti-inflammatory, anti-viral and/or anti-parasitic activity, each to a greater or lesser degree. The first of the cyclosporins to be identified was the fungal metabolite Cyclosporin A, or Ciclosporin, and its structure is given in The Merck Index, 11th Edition; Merck & Co., Inc.; Rahway, N.J., U.S.A. (1989) under listing 2759. Later cyclosporins to be identified are cyclosporins B, C, D and G which are also listed in The Merck Index under listing 2759. A large number of synthetic analogues are also known and representative examples are disclosed in EP 296 123, EP 484 281, and GB 2222770. Cyclosporin A and its structurally similar analogues and derivatives as well as metabolites thereof are generally referred to as "cyclosporins" for the purposes of this specification.

Ascomycins, of which FK-506 is the best known, are another class of generally immunosuppressive substances, also referred to as macrolide immunosuppressants. FK-506 is a macrolide immunosuppressant that is produced by *Streptomyces tsukubaensis* No. 9993. The structure of FK-506 is given in the appendix to The Merck Index, supra, as item A5. A large number of related compounds which retain the basic structure and immunological properties of FK-506 are also known. These compounds are described in various publications, for example EP 184162, EP 315973, EP 323042, EP 423714, EP 427680, EP 465426, EP 474126, WO 91/13889, WO 91/19495, EP 484935, EP 532088, EP 532089, WO 93/5059 and the like. Ascomycin, FK-506 and their structurally similar analogues and derivatives as well as metabolites thereof are termed collectively "ascomycins" in this specification.

Due to their extremely useful pharmaceutical properties, cyclosporins (Cyclosporins A and G in particular) and ascomycins (e.g., FK-506) have wide application in, for example the prevention of transplant rejection, in the treatment of auto-immune diseases such as rheumatoid arthritis and psoriasis, and also in the treatment of multi-drug-resistance. Cyclosporins and ascomycins also have certain side effects, the most notable being renal dysfunction, in particular nephrotoxicity, especially at higher doses. Nephrotoxicity is characterized by diminished renal blood flow and glomerular filtration with corresponding elevations in serum creatinine, alkaline phosphatase and urea as well as proximal cell swelling and necrosis and infiltration of macrophages. In some studies, hypoxia has been shown to damage proximal tubules rather selectively, and a decrease in blood flow could lead to hypoxia. Evidence has been presented implicating intracellular calcium in this pathology, and calcium channel blockers are effective in minimizing injury. However, $Ca^{++}$ channel blockers cannot be given without impunity. Accordingly, there is currently no known useful therapy for this important side effect on the kidney.

It has now surprisingly been found that glycine is suitable for prophylactic and/or therapeutic treatment of renal dysfunction induced by cyclosporins or ascomycins.

In accordance with the invention it has more particularly been found that dietary glycine inhibits and/or ameliorates one of the major side effects of chronic cyclosporin A administration-nephrotoxicity. Glycine prevents the decrease in glomerular filtration rate. Glycine also prevents the elevation in serum creatinine and urea, and tends to minimize the elevation in alkaline phosphatase due to cyclosporin A. The swelling and necrosis of proximal tubules and macrophage infiltration are also all prevented by dietary glycine. Thus, it is clear that glycine has a major protective action on nephrotoxicity due to cyclosporin A.

Figure 1:
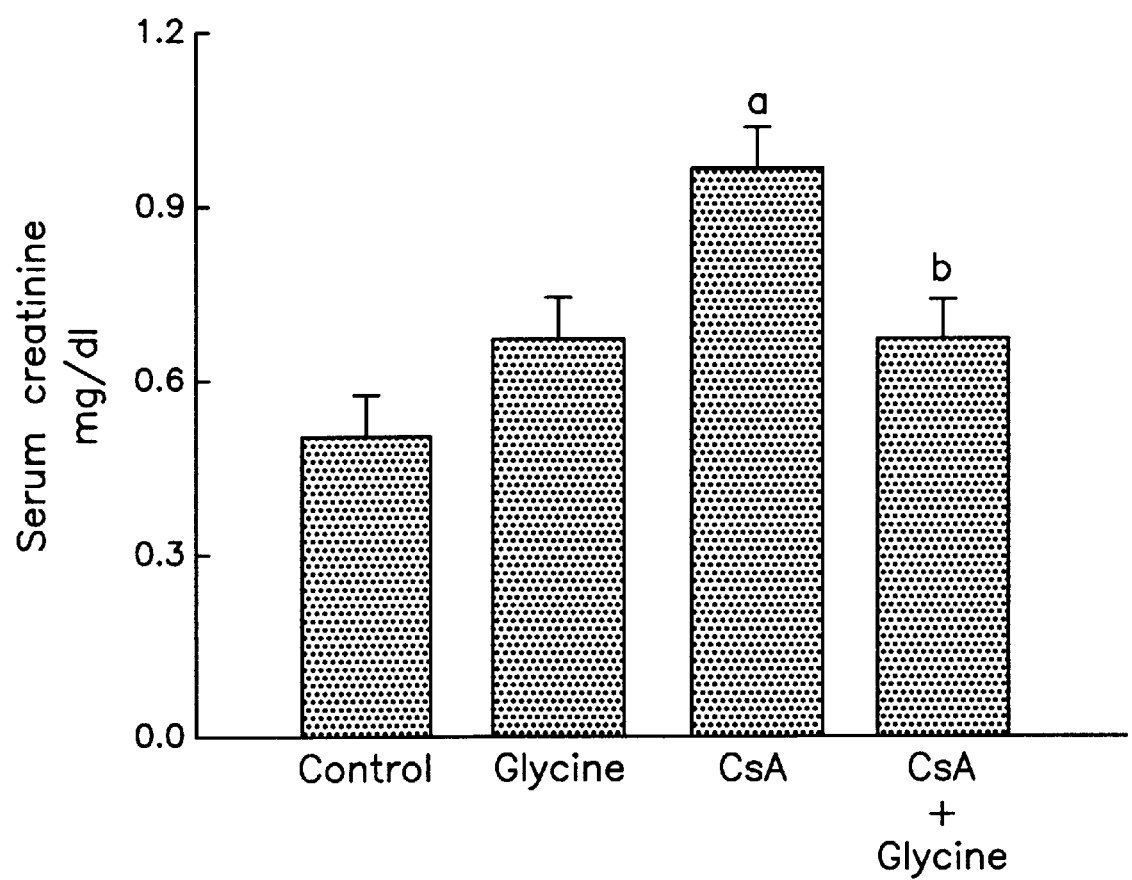
FIG. 1 is a bar graph depicting the mean serum creatinine levels (mg/dl) observed in four treatment groups of rats.

In view of the above-mentioned effects, there are medicaments and/or nutritional formulations comprising glycine as well as methods of using glycine. For use in the medicaments, nutritional formulations and methods of the invention, glycine is conveniently employed in free amino acid form (as opposed to salt form), in the form of glycine precursors, in particular alanine or serine (L-alanine, L-serine), likewise in free amino acid form, in physiologically acceptable salt form of said amino acids, or in form of mixtures of said amino acids and/or physiologically acceptable salts thereof. Glycine is preferably used in free amino acid form (as opposed to salt form), in physiologically acceptable salt form or in the form of a mixture of glycine in free amino acid form with glycine in physiologically acceptable salt form; most preferably glycine is in free amino acid form. Glycine may also be used in the form of dipeptides according to the invention.

This invention therefore provides the use of glycine in the preparation of a medicament or nutritional formulation for the prophylaxis and/or therapy of renal dysfunction induced by cyclosporins or ascomycins.

The invention further provides a method for the prophylactic and/or therapeutic treatment of renal dysfunction induced by cyclosporins or ascomycins comprising administering to a human being or other mammal prior to, simultaneous with, or subsequent to the treatment with a cyclosporin or ascomycin a medicament or nutritional formulation comprising glycine in an amount effective to inhibit and/or ameliorate the renal dysfunction.

Still further the invention provides a medicament or nutritional formulation comprising glycine for the prophylaxis and/or therapy of renal dysfunction induced by cyclosporins or ascomycins.

The invention also provides a medicament or nutritional formulation comprising a therapeutically effective amount of a cyclosporin or ascomycin in combination with glycine in an amount effective to inhibit and/or ameliorate the renal dysfunction induced by the cyclosporin or ascomycin.

Glycine is particularly useful in the prophylactic and/or therapeutic treatment of the renal dysfunction nephrotoxicity.

Glycine is further particularly useful for the therapy and/or prophylaxis of renal dysfunction induced by the cyclosporins cyclosporin A (Ciclosporin) and PSC 833 ([3'-desoxy-3'-oxo-MeBmt]$^1$[Val]$^2$-Ciclosporin, e.g. as described in EP 296 122), particularly by cyclosporin A.

Glycine is also particularly useful for the therapy and/or prophylaxis of renal dysfunction induced by the ascomycins FK-506 and ASM (33-epi-chloro-33-desoxy-ascomycin, e.g. as described in Ex. 66a of EP 427 680), particulary by FK-506.

Furthermore, glycine is particularly useful for the prophylaxis and/or therapy of renal dysfunction induced by immunosuppressive cyclosporins or ascomycins.

The nutritional formulation or medicanent may be administered to the patient enterally or parenterally. The enteral administration route is preferred. Particularly contemplated enteral administration routes are oral administration and/or tube feeding. The medicament or formulation is conveniently administered in the form of an aqueous liquid. The medicament or formulation in a form suitable for enteral application is accordingly preferably aqueous or in powder form, whereby the powder is conveniently added to water prior to use. For use in tube feeding, the amount of water to be added will depend, inter alia, on the patient's fluid requirements and condition. It will be appreciated that, for acute treatment, the parenteral application route is preferred.

The medicament or formulation may be so formulated as to deliver to the patient from 1 to 80 g, preferably 10 to 60 g, particularly preferred 15 to 30 g of glycine per 24 hours. The amount of medicament or formulation to be administered depends to a large extent on the patients' specific requirements. Such daily amounts of glycine are suitable for treatment of the desired effects as well as for prophylactic/pretreatment. The glycine comprising medicament or formulation may be administered to the patient in an amount such that the concentration of glycine in the patients' plasma is elevated to between 0.5 and 2.0 mM, preferably from 1.0 to 2.0 mM. Whilst concentrations higher than this are anticipated, it is expected that significant clinical effects will be obtained if the concentration of the acid is increased, as a consequence of administration of the formulation or medicament, so that it lies in the range of from 1.2 to 1.5 mM. In traumatic, hypercatabolic patients it may even be beneficial to raise the plasma glycine, serine or alanine levels to about 0.2 to 0.3 mM which corresponds to plasma glycine levels of healthy individuals.

Preferably the medicament or nutritional formulation comprises only glycine and optionally L-arginine or L-ornithine as free amino acids (as opposed to protein-bound or peptide-bound amino acids).

When glycine is administered in the form of a medicament such a medicament will comprise from 0.1 to 99 g of glycine per 100 g.

In general, favourable effects are obtained when administering glycine in the form of a nutritional formulation, which may, depending on the circumstances be a complete formula diet (i.e. a diet supplying essentially all required energy, amino acids, vitamins, minerals and trace elements) or a dietary supplement. A dietary supplement typically provides for 5 to 20% of the total daily calory intake, preferably about 10%. The nutritional formulation will conveniently be taken in aqueous liquid form. A nutritional formulation accordingly may comprise a source of carbohydrates, lipids fat (fat source) and/or protein (nitrogen source), and glycine, characterized in that glycine is present in the formula diet in an amount of about 0.2 to 60 g per 100 g dry weight of formula, preferably 5 to 45 g, particularly preferred 7.5 to 30 g per 100 g dry weight. The nutritional formulation will preferably further comprise other nutritionally advantageous components such as vitamins, minerals, trace elements, fibers (preferably soluble fibers). The amounts of carbohydrates lie in the range of 0–85% by weight, preferably 25 to 75% by weight, the amount of fat in the range of 0–30% by weight and the amount of protein in the range of 0–75% by weight, preferably 15 to 65%. Preferred nutritional formulations comprise the following: a dietary supplement consisting essentially of glycine and carbohydrates, a dietary supplement consisting essentially of glycine, carbohydrates and protein and/or a complete formula diet consisting essentially of glycine, carbohydrate, protein, fat, vitamins, minerals, trace elements and optionally fibers. Such dietary supplements or complete formula diets preferably further comprise L-arginine or other physiologically acceptable compound associated with the synthesis of nitric oxides such as Lornithine or glycerol, whereby L-arginine is preferred.

Examples of suitable nitrogen sources include nutritionally acceptable proteins such as soy bean or milk-derived proteins such as whey, caseinates or skim milk powder, and/or protein hydrolysates thereof. Suitable carbohydrate sources include all sugars, maltodextrins and starches. Examples of suitable fat sources include triglycerides, as well as di- and monoglycerides.

Examples of vitamins suitable for incorporation into the medicament or formulation of the invention include Vitamin E, Vitamin A, Vitamin D, Vitamin K, folic acid, thiamin, riboflavin, Vitamin $B_1$, $B_2$, $B_6$ and $B_{12}$, niacin, biotin and panthotenic acid in nutritionally acceptable form.

Examples of mineral elements and trace elements suitable for incorporation into the medicament or formulation include sodium, potassium, calcium, phosphorous, magnesium, manganese, copper, zinc, iron, selenium, chromium, and molybdenum in nutritionally acceptable form.

In particular, the medicament or formulation will preferably comprise beta-carotene (Vitamin A), Vitamin E, Vitamin C, thiamine, Vitamin $B_{12}$, choline, selenium and zinc in nutritionally acceptable form.

The term "soluble fiber" as used herein refers to fibers which are able to undergo substantial fermentation in the colon ultimately to produce short chain fatty acids. Examples of suitable soluble fibers include pectin, guar gum, locust bean gum, xanthan gum which may optionally be hydrolysed. For adults the total amount of soluble fibre per day will conveniently lie in the range of from 3 to 30 g.

It may be indicated to use glycine in combination with one or more of the following components:
  (i) omega-3 polyunsaturated fatty acids (PUFAs) where desired in admixture with omega-6 PUFAs;
  (ii) Larginine or other physiologically acceptable compound associated with the synthesis of nitric oxide, or mixtures thereof; and
  (iii) a nucleobase source.

Whereby the use of a medicament or nutritional formulation comprising glycine in combination with arginine or other physiologically acceptable compound associated with the synthesis of polyarnines such as ornithine is preferred. Use of a medicament or nutritional formulation comprising glycine, arginine or ornithine and omega-3 polyunsaturated fatty acids (PUFAs) is also preferred.

Nucleobase sources suitable for use in combination with glycine comprise or consist of natural nucleobases, nucleosides, nucleotides, RNA, DNA, equivalents thereof and/of mixtures comprising one or more of these compounds.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP), deoxythymidiylate (dTMP), deoxycytidylate (dCMP), and diphosphates and triphosphates of natural nucleosides such as ADP and ATP.

A purified nucleobase source, such as yeast is preferred. However, other sources such as meat and the like may be used. Preferably the nucleobase source is RNA.

Accordingly, the invention provides medicaments or nutritional formulations comprising effective amounts of:
  (a) glycine (component (a))
in association with one or more components selected from
  (b) omega-3 PUFAs where desired in admixture with omega-6 PUFAs (component (b));
  (c) L-arginine or other physiologically acceptable compound associated with the synthesis of nitric oxide, or mixtures thereof (component (c)); and
  (d) a nucleobase source (component (d)).

The dosage should be such that the medicaments or nutritional formulations are effective for the prevention and/or treatment of nephrotoxicity induced by macrolide immunosuppressive drugs.

One unit dose of such a medicament or nutritional formulation preferably comprises 1.5 to 80 parts by weight of component (a) in association with the following amounts of one or more components selected from (b) to (d): 0.1 to 20 parts by weight of component (b), 3 to 40 parts by weight of component (c) and 0.1 to 4.0 parts by weight of component (d). Particularly preferred one unit dose comprises 1.5 to 80 parts by weight of component (a) in association with the following amounts of one or more components selected from (b) to (d): 2 to 5 parts by weight of component (b), 7.5 to 20 parts by weight of component (c) and 1.7 to 2.0 parts by weight of component (d).

The amount of components (a) to (d) administered daily will conveniently correspond to 1.5 to 80 g for component (a), 0.1 to 20 g, preferably 2 to 5 g, for component (b), 3 to 40 g, preferably 7.5 to 20 g, for component (c) and 0.1 to 4.0 g, preferably 1.7 to 2.0 g, for component (d).

With respect to component (d) the above dosage is indicated for RNA, DNA, nucleosides or nucleotides. For nucleobases one weight unit of nucleobases is regarded to be equivalent to 2.5 to 3.0 weight units of RNA, DNA, nucleosides or nucleotides.

Where medicaments or nutritional formulations glycine in combination with one or more of the above-mentioned components (b), (c) and (d) are used, such medicaments or nutritional formulations will conveniently comprise in one unit dose (a) 1.5 to 80 parts by weight glycine,
in combination with one or more compounds selected from the group consisting of
  (b) 2 to 5 parts by weight omega-3 polyunsaturated fatty acids;
  (c) 7.5 to 20 parts by weight L-arginine, L-ornithine or glycerol, or mixtures thereof; and
  (d) 1.7 to 2.0 parts by weight RNA.

Preferred medicaments or nutritional formulations comprise in one unit dose:
  (a) from 1.5 to 80 parts by weight of glycine, in association with
  (c) 3 to 40 parts by weight, preferably 7.5 to 20 parts by weight, of arginine or an equivalent amount of one or more other physiologically acceptable compound associated with the synthesis of polyamines, or an equivalent amount of a mixture of arginine with such compound.

More preferably the medicaments or nutritional formulations of the invention comprise component (a) in combination with component (c) at a weight ratio of 1:2 to 4:1, particularly preferred at a weight ratio of 1:1 to 2:1.

Further preferred medicaments or nutritional formulations comprise in one unit dose:
  (a) from 1.5 to 80 parts by weight of glycine, in association with
  (b) 0.1 to 20 parts by weight, preferably 2 to 5 parts by weight, of omega-3 PUFAs; and
  (c) 3 to 40 parts by weight, preferably 7.5 to 20 parts by weight, of arginine or an equivalent amount of one or more other physiologically acceptable compound associated with the synthesis of polyamines, or an equivalent amount of a mixture of arginine with such compound.

Omega-3 PUFAs are conveniently protected against peroxidation during storage of the formulation.

Physiologically acceptable ways of protecting omega-3 PUFAs against peroxidation during storage are known in the art. They include physiologically acceptable micro-encapsulation of omega-3 PUFAs and the use of physiologically acceptable antioxidants in amounts sufficient to protect the fatty acids.

A typical example suitable for use as physiologically acceptable micro-encapsulation agents is starch. The micro-encapsulation can be effected in a manner known per se. The micro-encapsules may be coated in a manner known per se, by physiologically acceptable coating agents such as Gum Arabic.

Typical examples of antioxidants suitable for protecting fatty acids against peroxidation include antioxidant vitamins such as Vitamin C, Vitamin E or mixtures thereof.

The amount of antioxidant added should be sufficient to prevent peroxidation of the omega-3 PUFAs. Such amounts can be easily calculated. In general, for convenience, any antioxydants employed to prevent peroxidation, will be employed in excess. It will be appreciated that the presence of any other agent administered in association with the omega-3 PUFAs may require adjustment of the amount of antioxidant to be employed.

The omega-3 PUFAs may be employed in a form suitable for the physiological supply of omega-3 PUFAs, e.g. in free acid form, in triglyceride form, or in the form of physiologically acceptable natural sources of omega-3 PUFAs. Such natural sources include linseed oil and fish oils such as menhaden oil, salmon oil, mackerel oil, tuna oil, cod-liver oil and anchovy oil. Said natural sources, in particular, the fish oils, comprise substantial amounts of omega-3 fatty acids. Where the omega-3 PUFAs are employed in triglyceride form, said triglycerides may comprise esters with other physiologically acceptable fatty acids. Preferred omega-3 PUFAs include eicosapentaenoic acid (EPA) and docosahexaenoic acid (DHA), in free acid form, in triglyceride form or in form of natural sources having a high EPA and/or DHA content.

It will be appreciated that omega-3 PUFAs may be administered in higher amounts than those indicated hereinabove, and that such higher amounts will in general not impair the desired effect or provoke undesired side effects.

Compounds particularly suitable for use as component (c) in the formulation of the invention include L-arginine, glycerol and L-ornithine, most preferably L-arginine. Component (c) may be employed in free form, physiologically acceptable salt form, e.g. in the form of a salt with phosphoric acid, citric acid, tartaric acid, fumaric acid, adipic acid or lactic acid, or in small peptide form. Preferably L-arginine in free form is employed.

The term small peptides as used herein refers to peptides having from 2 to 6, preferably from 2 to 4 amino acids.

As already indicated, omega-3 PUFAs will conveniently be administered in the form of fish oils, protected or not against peroxidation. Such fish oils also comprises omega-6 PUFAs.

Omega-6 PUFAs have also a favourable effect on the immune response and on the resistance to infection upon surgery. Accordingly, diets of the invention will conveniently further comprise omega-6 PUFAs.

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention, include linoleic acid and arachidonic acid, linoleic acid being most preferred. Examples of suitable omega-6 PUFA sources are known in the art. They include fish oils and vegetable oils. Examples of omega-6 PUFA sources having a high linoleic acid content such as safflower oil, sunflower oil, soya oil, cotton oil and corn oil.

Administration of a daily amount of omega-6 PUFAs in the range of from 1.5 to 5.0 g will in general suffice to attain a favourable effect. One unit dose of the medicaments or nutritional formulation defined above may accordingly further contain 1.5 to 5 parts by weight of omega-6 PUFAs.

In addition to components (b), (c) and (d), and omega-6 PUFAs further components may be added to the diets of the invention and may have a beneficial effect on the activity of glycine. An example of such beneficial components are omega-9 PUFAs. A preferred natural source for such fatty acid mixtures are fish oils. For taste and other reasons, the fish oils will, in oral application forms, preferably be used in encapsulated form.

Where the nutritional formulation of the invention is intended for use as a dietary supplement, the amount of energy supplied by it should not be too excessive, in order not to unnecessarily suppress the patients appetite. The supplement should conveniently comprise energy sources in an amount supplying from 150 to 1000 Kcal/day, preferably 250 to 500 Kcal/day. The contribution of the nitrogen source, carbohydrate source and lipid source to the total daily caloric may vary within wide ranges. For use as a supplement, the administration may be in powder or liquid form.

The treatment period will coincide with the treatment with the immunosuppressive drug.

The dietary supplement will conveniently be administered in the form of unit doses suitable for administration of the supplement 1 to 4 times per day. Where the nutritional formulations comprise energy sources, it is appropriate not to supply more than 1000 Kcal/day. Apart from this limitation with respect to the energy supply, nutritional formulations for preventing and/or treating nephrotoxicity induced by macrolide immunosuppressive drugs can and will conveniently be supplied in the form of formula diets or dietary supplements as described above.

Typical pharmacologically acceptable formulation forms (medicaments) for oral administration will further comprise pharmacologically acceptable diluents, carriers, vitamins, spices, pigments and/or other adjuvants well known to the skilled person to be suitable for incorporation into such formulation and optionally a macrolide immunosuppressive drug.

The diets and formulations of the invention may be obtained in a manner known per se, e.g. by admixing the ingredients.

The invention is further illustrated by the following Examples which are not intended in any way to limit the scope of the claimed invention.

EXAMPLE 1

Animal and Diets

Male Sprague-Dawley rats (Sasco) weighing approximately 200 g were fed a synthetic powdered diet containing 5% glycine and 15% casein (glycine) or 20% casein (control) for 3 days prior to initiation of cyclosporin A treatment. Components of the powdered diet are shown in Table 1. All animals were given humane care in compliance with institutional guidelines. After the prefeeding period, cyclosporin A (25 mg/kg soluted as 2.5 mg/ml in olive oil) or vehicle was given daily by oral gavage for approximately 4 weeks. Four groups of 6–8 rats each (control, glycine, cyclosporin+control, cyclosporin+glycine) were studied. Animals weight and diet consumption was measured daily.

TABLE 1

Composition of Control and Glycine Diets

| Component | Control | Glycine |
| --- | --- | --- |
| Casein | 20.0 | 15.0 |
| Glycine | 0.0 | 5.0 |
| Sucrose | 50.0 | 50.0 |
| Corn oil | 5.0 | 5.0 |
| Cellulose | 5.0 | 5.0 |
| Mineral mix | 3.5 | 3.5 |
| Vitamin mix | 1.0 | 1.0 |
| DL-Methionine | 0.3 | 0.3 |
| Choline bitartrate | 0.2 | 0.2 |
| Corn starch | 15.0 | 15.0 |

Glomerular Filtration Rate and Clinical Chemistry

Animals were placed in metabolic cages 48–72 hours prior to sacrifice, 24 hour urine samples were collected and 0.5 ml of blood was drawn from the tail vein for blood creatinine measurements. On the day of sacrifice, another 1 ml of blood was drawn from the vena cava and replaced with an equal volume of Ringers lactate-solution. Serum urea (Coulombe, J. J. and L. Favreau. 1963. A new simple semimicro method for colorimetric determination of urea. Clin. Chem. 9:102–108); and creatinine (Heinegard, D. and G. Tiderstrom. 1973. Determination of serum creatinine by a direct colorimetric method. Clin. Chim. Acta.

43:305–310); as well as urine creatinine were measured using Sigma kits while serum alkaline phosphatase was measured enzymatically (blood samples were collected after approx. 4 weeks of cyclosporin A treatment). Glomerular filtration rate was calculated from the ratio of creatinine in the urine/blood (Laiken, N. D. and D. D. Fanestil. 1985. Filtration and Blood Flow. In Physiological basis of medical practice. J. B. West, editor. Williams & Wilkins, Baltimore/London. 461–471), urine samples were collected after approx. 4 weeks of cyclosporin A treatment.

Histology

On the day of sacrifice animals were anesthetized with pentobarbitol (50 mg/1g), the abdomen was opened and the aorta was canulated with a 24 French i.v. canula with the lip placed near the renal arterial branches. The aorta was clamped above and ligated beneath the renal branches and the left kidney was rinsed with 5 ml normal saline and perfusion-fixed with 4% paraformaldehyde solution in phosphate buffered saline. The kidney was removed, cut in 0.5 thick slices and placed in 10% formaline. Hemtoxyllin-eosin sections were performed and analyzed microscopically. Dilated tubules were counted in 5 different low power fields (100x), necrotic cells and infiltrating macrophages were counted in 5 different tubules at high power magnification (400x) and averages±SEM calculated.

Quantitation of Neutrophils

Blood smears were prepared from vena cava samples on the day of sacrifice and stained with Wright Giemsa stain. Differential white blood cell counts for 200 white blood cells were performed at high power magnification (400x) and percentages calculated.

Statistics

For all statistics, one-way ANOVA and the Bonferonni post-hoc test was used. p<0.05 was selected prior to the study to indicate significance.

RESULTS

Clinical Chemistry and Glomerular Filtration Rate

It is known that cyclosporin A elevates serum urea. Indeed, urea was increased over 70% in this study (Table 2). While glycine tended to minimize this increase, the effect was not statistically significant. Cyclosporin A also increased alkaline phosphatase (Table 2), and glycine tended to prevent the increase. Serum creatinine ranged from 0.4–0.6 mg/dl in the control and glycine treated groups (FIG. 1) but was doubled significantly by cyclosporin A. This increase was prevented totally by the glycine diet. Values are means±S.E.M. (P<0.01 by ANOVA; n=5–6 in each group). a,p<0.05 compared to control; b,p<0.05 compared to the cyclosporin A group.

Figure 2:
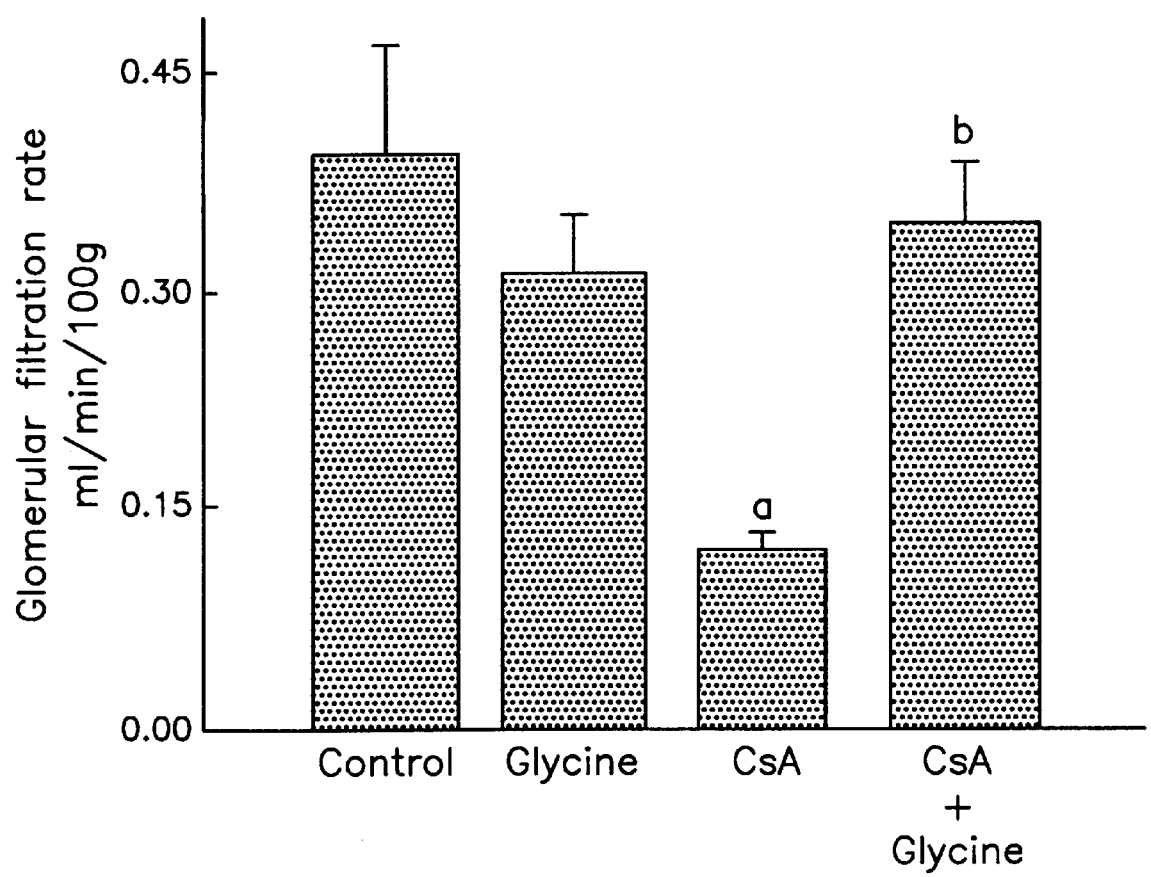
FIG. 2 is a bar graph depicting the mean glormerular filtration rate observed in each of the treatment groups following four weeks of treatment.

It is also known that cyclosporin A diminishes glomerular filtration rate. In this study, values in the cyclosporin A group were about 30% of those of control or glycine alone groups (FIG. 2). This decrease in glomerular filtration rate was also totally prevented by glycine in the diet. A diet comprising 1% of the total caloric content as glycine was already sufficient to give this effect (results not shown). Values are means±S.E.M. (P<0.01 by ANOVA; n=5–6 in each group). a,p<0.05 compared to control; b,p<0.05 compared to the cyclosporin A group. Significant changes in urine volume were also noted (control, 9.1±1.6 ml/24 h; glycine, 6.7±0.8; cyclosporin A, 14.4±2.3; glycine+cyclosporin A, 11.8±2.1).

TABLE 2

Effects of Cyclosporin A and a Glycine Diet on Serum Urea and Alkaline Phosphotase Levels

| | Urea (Mg/dl) | Alkaline Phosphotase (UL) |
|---|---|---|
| Control | 21.8 ± 1.8 | 46.5 ± 4.4 |
| Glycine | 20.6 ± 2.4 | 33.1 ± 5.6 |
| Cyclosporin A | 34.9 ± 3.7[a] | 65.9 ± 12.6 |
| Cyclosporin A + glycine | 31.2 ± 0.6[a] | 47.7 ± 8.8 |

Values are mean ± S.E.M.; a, p < 0.05 compared to controls by ANOVA and Student-Newman-Keuls test (n = 5–6 in each group)

Histology and White Blood Cells

Figure 3A:
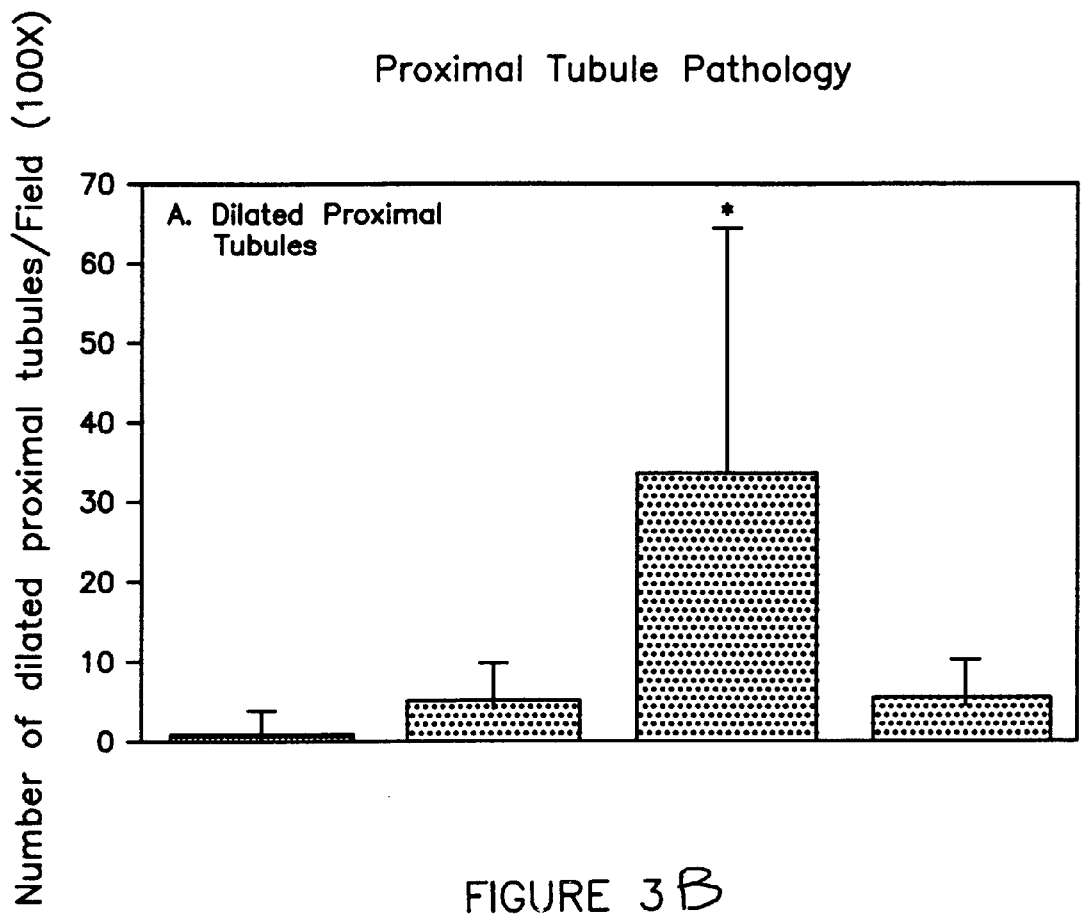
FIG. 3A is a bar graph depicting the mean number of dilated proximal tabules per slide observed in each of the treatment groups under low power (100x).
Figure 3B:
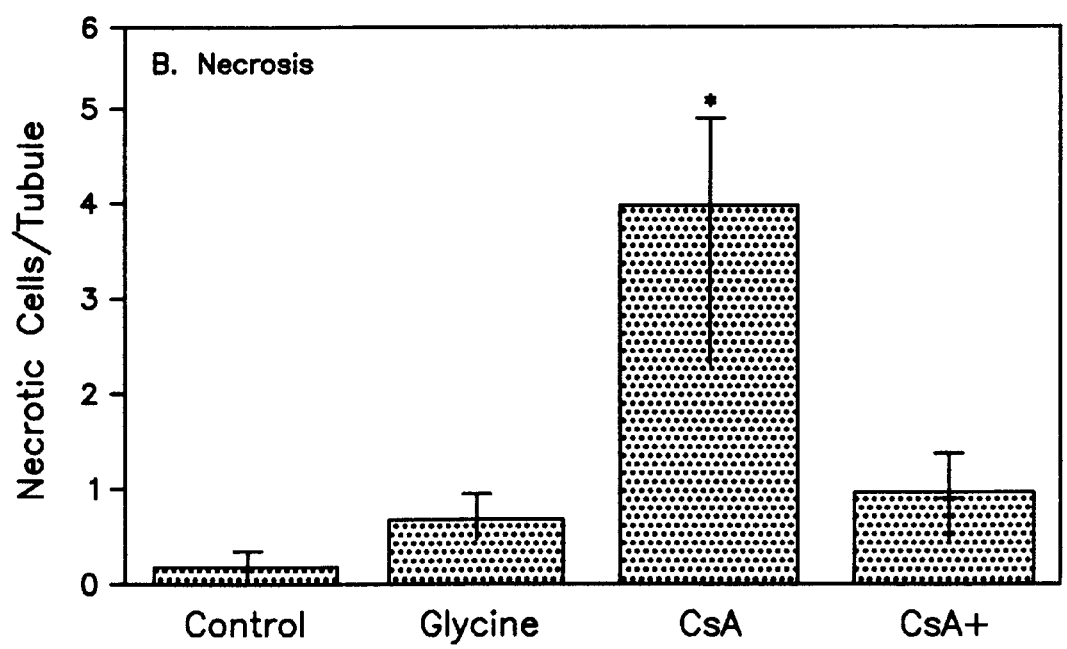
FIG. 3B is a bar graph depicting the mean number of necrotic cells in each of the treatment groups counted on five different tubules per slide under high power (400x).
Figure 4:
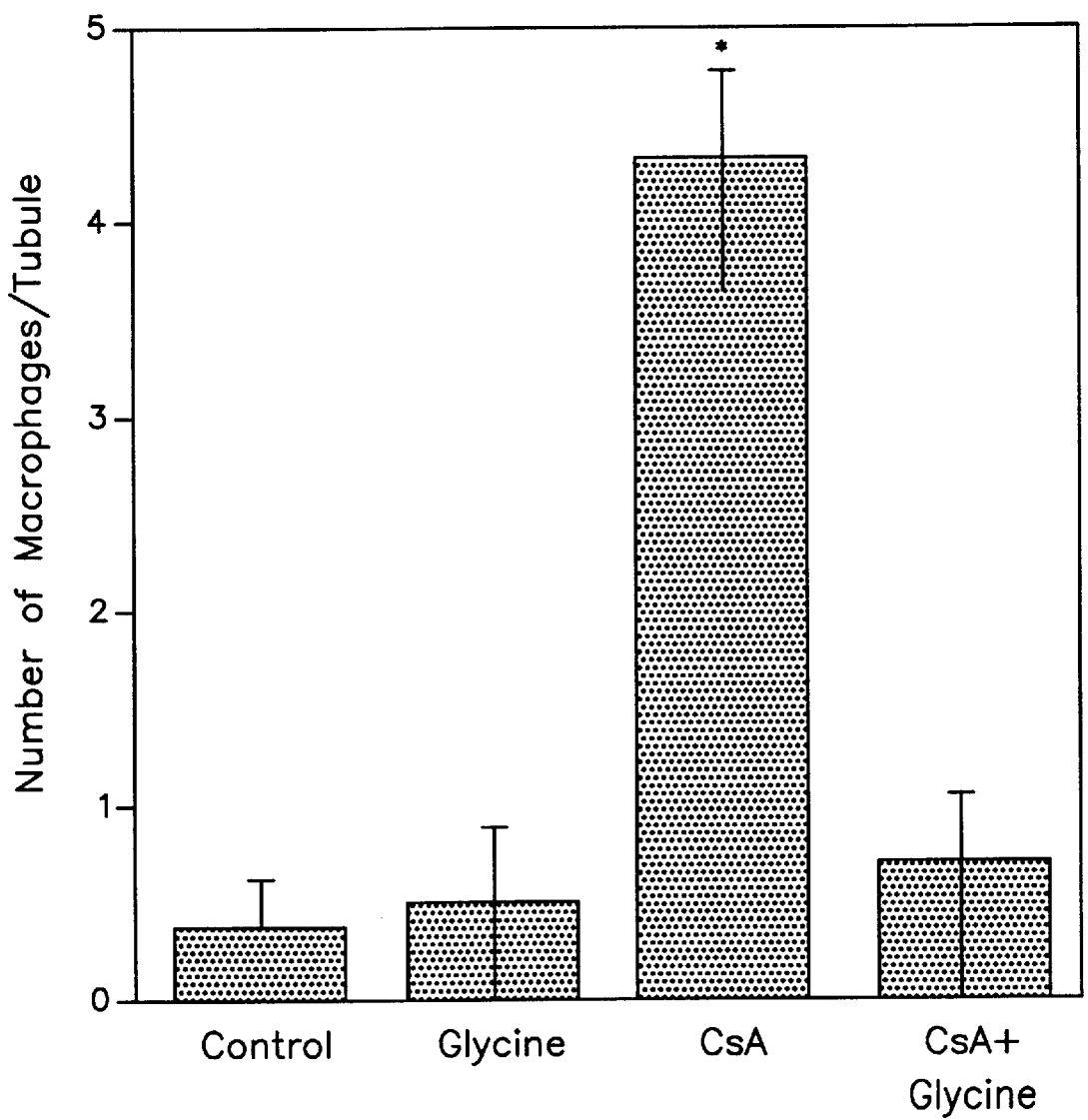
FIG. 4 is a bar graph depicting the mean number of macrophages observed proximate to 5 different tubules per slide under high power (400x).
Figure 5:
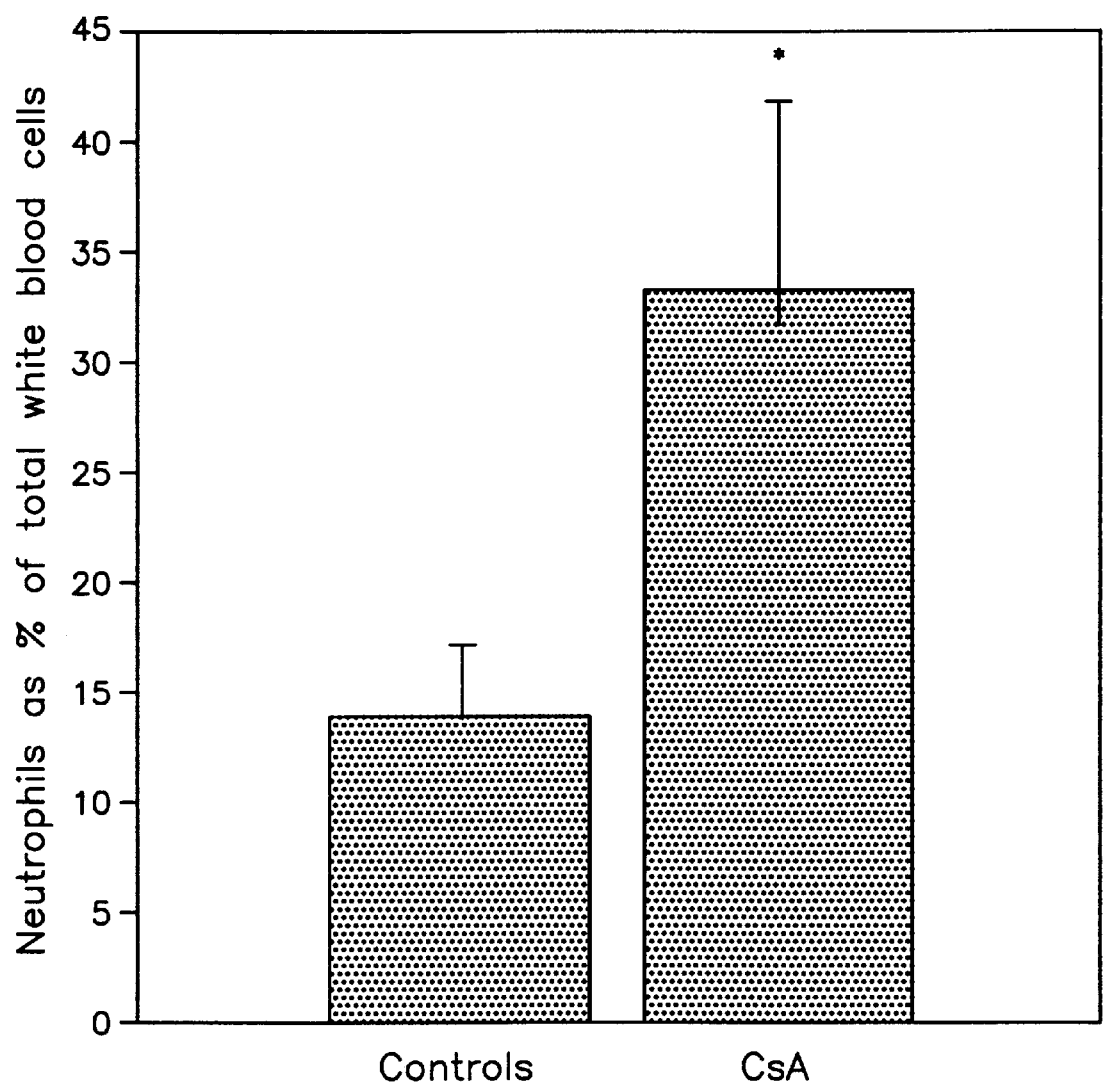
FIG. 5 is a bar graph depicting the percentage of neutrophils found as a function of the total number of white blood cells in the control and CsA treatment groups.

It is clear that cyclosporin A causes proximal tubular swelling and necrosis with associated white blood cell infiltration as has been reported previously.These effects were totally prevented by the glycine-containing diet. On average, proximate cell swelling and necrosis as well as infiltrating macrophages were elevated significantly by cyclosporin A (FIGS. 3, 4). Dilated proximal tubules (panel A of FIG. 3) were counted in three different low power fields per slide (magnification 100x) and average±S.E.M. calculated. Necrotic cells (panel B of FIG. 3) were counted on five different tubules per slide at high power (400x) (mean±S.E.M.*=p<0.05 by ANOVA). In FIG. 4 macrophages were counted around 5 different tubules per slide at high magnification (400x) in hematoxyllin-eosin stained sections by a reviewer blinded to treatment and averages±S.E.M. calculated (*=p<0.05 by ANOVA). Further, there was a nearly 3-fold increase in neutrophils in blood smears from cyclosporin A treated rats (FIG. 5). Blood smears were stained with Wright Giemsa stain and differential cell counts were performed (*=p<0.05 by ANOVA).

EXAMPLE 2

Enteral Compositions

In the following compositions MM stands for "mineral mixture", SM for "trace element mixture" and VM for "vitamin mixture". The composition of these three mixtures is as follows:

| Ingredients | g/100 g |
|---|---|
| MM | |
| Maltodextrins | 34.40 |
| K citrate/phosphate | 34.60 |
| Magnesium dicitrate | 8.20 |
| Calcium chloride | 8.00 |
| Sodium citrate/chloride | 9.00 |
| Citric acid | 3.50 |
| Choline tartrate | 2.30 |
| SM | |
| Maltodextrins | 47.79 |
| Molybdenum-yeast | 18.00 |
| Chromium-yeast | 9.20 |
| Zinc sulfate | 7.00 |
| Selenium-yeast | 7.00 |
| Ferrum(II) sulfate | 6.92 |
| Copper(II) gluconate | 2.24 |
| Manganese(II) sulfate | 1.12 |
| Sodium fluoride | 0.70 |
| Potassium iodide | 0.03 |
| VM | |
| Maltodextrins | 43.44 |
| Sodium ascorbate | 35.00 |
| Vitamin E-Ac. 50% | 16.00 |

| Ingredients | g/100 g |
|---|---|
| Niacinamide | 1.55 |
| Vitamin A-Acetate | 1.20 |
| Ca-D-Panthothenat | 0.98 |
| Vitamin $K_1$ 1% | 0.71 |
| Vitamin $B_{12}$ 0.1% | 0.30 |
| Vitamin $D_3$ | 0.28 |
| Vitamin $B_6$ | 0.20 |
| Vitamin $B_1$ | 0.17 |
| Vitamin $B_2$ | 0.15 |
| Folic acid | 0.02 |
| Biotin | 0.01 |

Composition I Comprising Glycine

| Ingredients | g/100 g |
|---|---|
| Water | 77.40 |
| Maltodextrins | 12.28 |
| Na/Ca caseinates | 4.60 |
| Glycine | 3.00 |
| Lipids: | |
| Palm oil | 2.33 |
| Sunflower oil | 0.26 |
| Emulsifier Nathin E | 0.13 |
| | 100.00 |

Composition II Comprising Glycine

| Ingredients | g/100 g |
|---|---|
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |

Composition Comprising Glycine and Arginine

| Ingredients | g/100 g |
|---|---|
| Water | 77.40 |
| Maltodextrins | 8.93 |
| Na/Ca caseinates | 4.60 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 2.36 |
| Sunflower oil | 0.23 |
| Emulsifier Nathin E | 0.13 |
| | 100.00 |

Composition Comprising Glycine and Fish Oil (ω-3 fatty acids)

| Ingredients | g/100 g |
|---|---|
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

Composition Comprising Glycine and RNA

| Ingredients | g/100 g |
|---|---|
| Water | 77.40 |
| Maltodextrins | 9.96 |
| Na/Ca caseinates | 4.60 |
| Glycine | 3.00 |
| Yeast extract RNA | 0.14 |
| MM | 2.00 |
| SM | 0.05 |
| VM | 0.10 |
| β-Carotine | 0.03 |
| Palm oil | 2.33 |
| Sunflower oil | 0.26 |
| Emulsifier Nathin E | 0.13 |
| | 100.00 |

Composition Comprising Glycine, Arginine and Fish Oil (ω-3 fatty acids)

| Ingredients | g/100 g |
|---|---|
| Water | 77.40 |
| Maltodextrins | 8.93 |
| Na/Ca caseinates | 4.60 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

Composition Comprising Glycine, Arginine and RNA

| Ingredients | g/100 g |
|---|---|
| Water | 77.40 |
| Maltodextrins | 8.79 |
| Na/Ca caseinates | 4.60 |
| Glycine | 3.00 |
| Arginine | 1.17 |
| Yeast extract RNA | 0.14 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |

Composition Comprising Glycine, RNA and Fish Oil (ω-3 fatty acids)

| Ingredients | g/100 g |
|---|---|
| Water | 77.40 |
| Maltodextrins | 9.96 |
| Na/Ca caseinates | 4.60 |
| Glycine | 3.00 |
| Yeast extract RNA | 0.14 |
| MM | 2.00 |
| SM | 0.05 |
| VM | 0.10 |
| β-Carotine | 0.03 |
| Lipids: | |
| Palm oil | 1.32 |
| Sunflower oil | 0.23 |

-continued

| Ingredients | g/100 g |
|---|---|
| Emulsifier Nathin E | 0.13 |
| Fish Oil EPAX 3000 TG | 1.04 |
| | 100.00 |
| Composition Comprising Glycine, Arginine, RNA and Fish Oil (ω-3 fatty acids) | |
| Water | 77.40 |
| Maltodextrins | 8.79 |
| Na/Ca caseinates | 4.60 |
| Glycine | 3.00 |
| Arginine | 1.17 |
| Yeast extract RNA | 0.14 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

As already set out above fish oil is a natural source for omega-3 PUFAs whereas sunflower oil is a natural source for omega-6 PUFAs.

What is claimed is:

1. A method for the prophylactic and/or therapeutic treatment of renal dysfunction induced by cyclosporins or ascomycins comprising enterally administering to a human being or other mammal simultaneous with the treatment with a cyclosporin or ascomycin, a medicament or nutritional formulation comprising an amino acid component consisting essentially of glycine in an amount effective to inhibit and/or ameliorate the renal dysfunction, a carbohydrate source, and optionally one or more components selected from vitamins, minerals, trace elements, and fibers.

2. The method of claim 1 wherein the nutritional formulation is a dietary supplement.

3. The method of claim 2 wherein the dietary supplement consists essentially of glycine and a carbohydrate source.

4. The method of claim 3 wherein the dietary supplement further comprises a protein source.

5. The method of claim 1 wherein the nutritional formulation is a complete formula diet.

6. The method of claim 1 wherein the medicament further comprises a cyclosporin or ascomycin.

7. An enteral medicament or nutritional formulation comprising a therapeutically effective amount of a cyclosporin or ascomycin in combination with an amino acid component consisting essentially of glycine in an amount effective to inhibit and/or ameliorate the renal dysfunction induced by said cyclosporin or ascomycin, and 25 to 75% carbohydrate by weight of the medicament or nutritional formulation, and one or more components selected from vitamins, minerals and trace elements, wherein glycine is present in an amount of about 0.2 to 60 g per 100 g dry weight of the medicament or nutritional formulation.

8. The enteral medicament or nutritional formulation of claim 7 which comprises one or more vitamins selected from beta-carotene, Vitamin E, and Vitamin C.

9. The enteral medicament or nutritional formulation of claim 7 which comprises selenium.

10. The enteral medicament or nutritional formulation of claim 7 which comprises fat and/or protein.

11. The method of claim 2 wherein the dietary supplement comprises 0.2 to 60 g glycine per 100 g dry weight and 25 to 75% by weight carbohydrates.

12. The method of claim 2 wherein the dietary supplement comprises 5 to 45 g glycine per 100 g dry weight and 25 to 75% by weight carbohydrates.

* * * * *